US00PP37344P2

(12) United States Plant Patent
Hansen

(10) Patent No.: US PP37,344 P2
(45) Date of Patent: Mar. 24, 2026

(54) ***HEMEROCALLIS* PLANT NAMED 'Rule of Plum'**

(50) Latin Name: ***Hemerocallis* (L.) hybrid**
Varietal Denomination: Rule of Plum

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,945

(22) Filed: Dec. 2, 2025

(51) Int. Cl.
*A01H 6/00* (2018.01)
*A01H 5/02* (2018.01)

(52) U.S. Cl.
USPC ..... Plt./312

(58) Field of Classification Search
USPC ..... Plt./312
CPC ..... A01H 6/00; A01H 5/02
See application file for complete search history.

*Primary Examiner* — Keith O. Robinson

(57) ABSTRACT

A new and distinct *Hemerocallis* plant named 'Rule of Plum' characterized by winter-hardy compact habit with clean medium-green foliage that goes dormant in the winter. The flowers are single, rounded, lightly fragrant, deep purple with a yellow-green throat. Inner tepals are reflexed with slightly crisped margins. The new plant flowers on stems up to 57 cm tall with four-way branching beginning about mid-July.

2 Drawing Sheets

Botanical classification: *Hemerocallis* (L.) hybrid.
Variety denomination: 'Rule of Plum'.

STATEMENT REGARDING PRIOR DISCLOSURES UNDER 37 CFR 1.77(B)(6)

The new cultivar was registered in 2025 with the American Daylily Society which is the International Cultivar Registration Authority for the genus *Hemerocallis* with a brief description and photograph. No plants of *Hemerocallis* 'Rule of Plum' have been sold or offer for sale in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct daylily plant, *Hemerocallis* 'Rule of Plum' hereinafter also referred to as the new plant or just the cultivar name 'Rule of Plum'. *Hemerocallis* 'Rule of Plum' was hybridized by the inventor on Jul. 23, 2013, in a greenhouse at a wholesale perennial nursery in Zeeland, Michigan, USA. The new plant originated from a breeding program conducted by the inventor with the specific intention to improve the garden worthiness, expand color regimens and increase flowering period which were some of the criteria of further trials in the trial beds at the same nursery in Zeeland, MI. The female or seed parent was 'Pardon Me' (not patented) and the male or pollen parent was 'Alpine Mist' (not patented).

The new plant was selected as a single seedling from this cross, and during confidential evaluations in a trial bed beginning in 2015 at the same nursery was assigned the breeder code 13-141-1. The new plant has been asexually propagated by division at the same nursery since 2015 with all resultant asexually propagated plants having retained all the same unique traits as the original plant. *Hemerocallis*

'Rule of Plum' is stable and reproduces true to type in successive generations of asexual reproduction.

There are over 110,000 daylilies registered with The American *Hemerocallis* Society, which is the International Cultivar Registration Authority for the genus *Hemerocallis*. In comparison to the new plant, the female parent has a brighter cranberry-red flower color with a yellow watermark and a green throat on shorter scapes. In comparison to the new plant, the male parent has a lavender purple flower with washed bluish-lavender eye zone and yellow green throat on short scapes.

The most similar daylily cultivars known to the inventor are: 'All Yours' (not patented), 'Cinderella's Dark Side' (not patented), 'Forsyth Jimny Cricket' (not patented), 'John Henry Reeves' (not patented), 'Little Blackie' (not patented), 'Midnight Chase' (not patented), 'Midnight Oil' (not patented), 'Purple de Oro' (not patented), 'Purple Sphere' (not patented), 'Remus' (not patented), and 'Spirit World' (not patented).

'All Yours' has slightly taller scapes and larger flowers with tepals that are deeper burgundy and flowers earlier in the season. 'Cinderella's Dark Side' has taller scapes producing flowers that are deeper maroon-black with a darker black-purple eye more green throat. 'Forsyth Jimny Cricket' has larger flowers with less recurved inner tepals, and the eye is larger and more violet-black. 'John Henry Reeves' has larger flowers with flatter and narrower tepals, the eye is darker violet and the throat is more green. 'Little Blackie' has slightly shorter scapes, and slightly larger flowers with larger eyes of darker purple. 'Midnight Chase' has slightly taller scapes producing larger flowers of dark purple with yellow-green throat, and less recurved inner tepals. 'Midnight Oil' has taller scapes with larger flowers of darker black-purple and more intense green throat. 'Purple de Oro' has a shorter scape with flowers of medium purple and lighter purple midrib and gold throat. 'Purple Sphere' has larger flowers of violet purple, broader inner tepals, and a greenish-white throat. 'Remus' has taller scapes and the inner tepals are broader and more longitudinally pinched toward apex. 'Spirit World' has taller scapes, flowers with a larger green throat, and the inner tepals are broader with a slightly lighter purple midrib.

*Hemerocallis* 'Rule of Plum' differs from all other daylilies known to the applicant, by the combination of the following traits:

1. Winter-hardy, compact habit with clean medium-green foliage that goes dormant in the winter;
2. Lightly fragrant, single, rounded flowers about 8 cm across of deep purple with a yellow-green throat;
3. Inner tepals reflexed with slightly crisped margins.
4. Flowering begins about mid-July with excellent coverage with occasional repeat flowering late in the season;

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
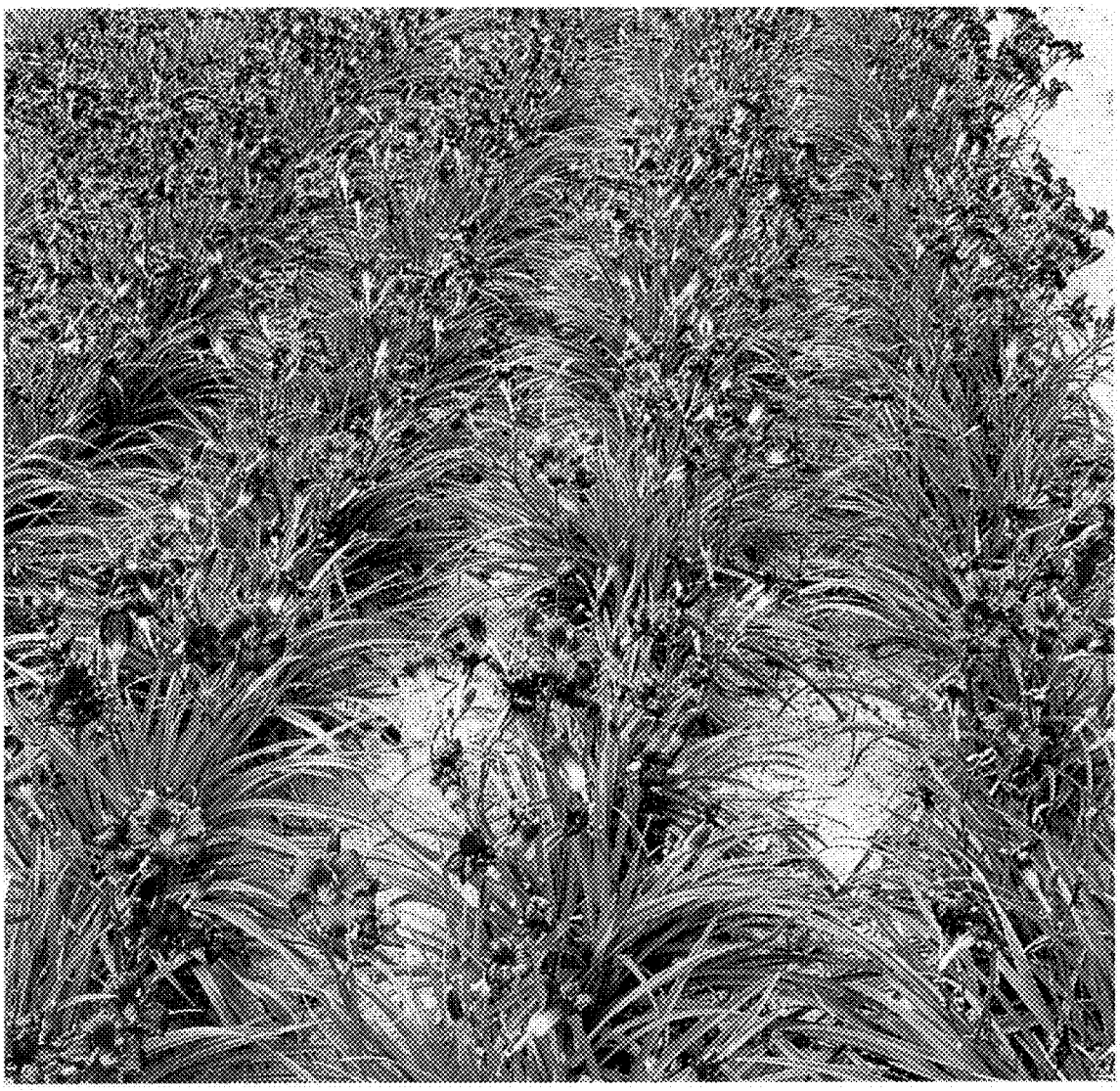
FIG. 1 shows a group of two-year-old plants in peak flower in a sunny production field near Zeeland, Michigan.
Figure 2:
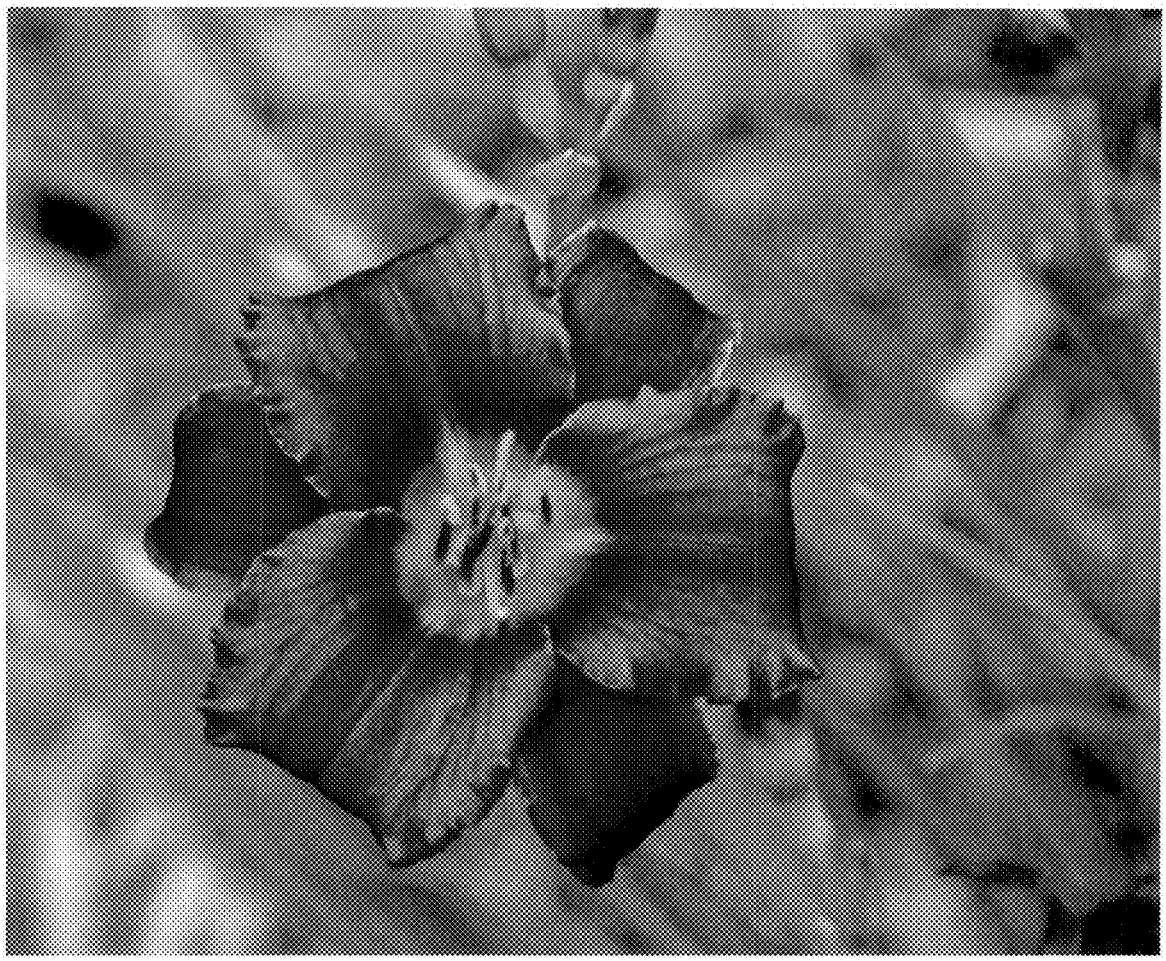
FIG. 2 shows a close-up of the flower.

The following descriptions and color references are based on the 2015 edition of The. Royal Horticultural Society Colour Chart except where common dictionary terms are used. The new plant, *Hemerocallis* 'Rule of Plum', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Michigan with and supplemental water and fertilizer.

Botanical classification: *Hemerocallis* (L.) hybrid;

Parentage: Female or seed parent is 'Pardon Me'; male or pollen parent is 'Alpine Mist';

Propagation: Division of the rhizome;

Growth rate: Moderate to rapid;

Crop time: About 8 to 10 weeks to flower starting in spring in a 3.8-liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with seven to ten basal shoots emerging from rhizomes producing a radially symmetrical mound of arching leaves;

Plant size: Foliage height about 45 cm tall from soil line to the top of the leaves and about 68 cm wide at the widest point; flowering to about 57 cm tall;

Leaves: Linear; apex narrowly acute; base sheathing, sessile; entire; glabrous, slightly glaucous adaxial and abaxial becoming matte; folded, equitant, basal; about 13 leaves per division; Leaf aspect: arching in outer leaves to erect in inner leaves;

Leaf size: To about 40 cm long and 2 cm across, average about 34 cm long and about 1.7 cm across;

Cauline leaves: About 2 per scape about one-third of the way up the peduncle to flowers; reduced, to about 6.5 cm long and 1.4 cm wide, average about 4.8 cm long and 1.2 cm wide;

Leaf color: Cauline and young basal adaxial and abaxial nearest RHS 144A; mature cauline and basal leaves adaxial nearest RHS 146B and abaxial nearest RHS 146A;

Veins: Parallel; color adaxial nearest RHS 146B and abaxial nearest RHS 146A;

Flower description:

Flowers: Funnelform; single, with two sets of three tepals; zygomorphic, incomplete; aspect upward and outwardly; about 8 cm across and 7 cm tall to exserted stigma, corolla about 5 cm deep; corolla tube diameter at fusion about 1.1 cm, length from base to fusion point about 1.8 cm long; individually lasting for about one day; peduncle remains effective from mid-July into mid-August for approximately four weeks in Zeeland, Michigan;

Inflorescence: Upwardly, erect; stiff; slightly glaucous; glabrous; branched; to about 57 cm tall; flowering in the upper 20 cm and to about 15 cm across; with two to three branches and to about 13 flowers;

Flower fragrance: Very slight, lightly sweet;

Buds about one day prior to opening: Oblong ellipsoid; bluntly acute apex, proximal 1.7 cm narrowed terete; base rounded; about 6.5 cm long and about 1.9 cm in diameter at widest point with proximal 1.7 cm narrowing to about 0.5 cm diameter;

Bud color one day from opening: Barrowed base between RHS N144B and RHS 154A, proximal portion of inflated bulb portion between RHS N144D and RHS 151C, distal portion of inflated bulb between RHS 187B and RHS 177A;

Tepals: 2 sets of 3;

Inner tepals: Broadly ovate; glabrous; rounded apex; base truncate, fused in proximal 18 mm; with moderate narrow margin undulation; margin entire and moderately undulate; midrib furrowed about 2 mm wide on abaxial and slightly costate on adaxial surface; apical 20 mm reflexed about 270° to 360°; width at fusion about 8 mm, about 38 mm across at widest point and about 78 mm long;

Inner tepal color: Adaxial distally nearest RHS 187B with veins nearest RHS 187A, proximal throat nearest RHS N144A and distal throat nearest RHS 9A, basal midrib between RHS 186B and RHS 186A; abaxial apical 1 mm to 2 mm nearest RHS N186A, next distal one-third to one-half portion between RHS 185C and RHS 186A, middle portion between RHS 151D and RHS 9B, and proximal one-third including fused portion nearest RHS N144D;

Outer tepals: Narrowly ovate to oblanceolate; glabrous; rounded apex; base truncate, fused in proximal 18 mm; margin entire and flat; midrib not obvious; reflex about 270° in the distal 20 mm; width at fusion about 9 mm, about 25 mm across at widest point, and 75 mm long;

Outer tepal color: Adaxial distal one-half between RHS 187C and RHS 187B, proximal throat nearest RHS N144A and distal throat nearest RHS 9A; abaxial apical 1 mm to 2 mm nearest RHS 146A, next distal one-third to one-half portion nearest RHS 186A on the margin and the longitudinal center between RHS 185C and RHS 176B, middle portion between RHS 151D and RHS 9B, and proximal one-third including fused portion nearest RHS N144D;

Pedicel: Cylindrical; glabrous; slightly lustrous; from 8 mm to 12 mm long and 2 mm diameter; aspect upward to slightly outwardly;

Pedicel color: Between RHS 144A and RHS 146A;

Peduncle: Cylindrical; glabrous; slightly glaucous; to 3 per plant, average about 1.5 peduncles per plant; erect to about 51 cm tall and 0.5 cm diameter at base, average about 49 cm tall and 0.5 cm diameter; extending above foliage;

Peduncle color: Nearest RHS 137D;

Gynoecium: Single; tri-carpelled; glabrous; about 7.2 cm long;

*Style*.—Single; cylindrical; slightly lustrous; about 6.3 cm long, 1 mm diameter before stigma and 1.5 mm diameter at base, arcuate slightly upward at distal one-third; color distally nearest RHS 187B, middle nearest RHS 19D, and proximally nearest RHS 4D.

*Stigma*.—Globose; 1 mm diameter; color nearest RHS 162B.

*Ovary*.—Conical; lightly longitudinally furrowed distally; acute apex, truncate base; about 6 mm long and 4 mm diameter at base; color nearest RHS 145A.

Androecium: Six; glabrous; proximally adnate to inner corolla;

*Filaments*.—Six; cylindrical distally, slightly applanate proximally; lustrous; arcuate slightly upward in distal one-third; adnate to inner tepal in basal 19 mm above ovary; free in distal 40 mm long from fusion point on tepal; to about 59 mm long, 3 mm across and 2 mm thick near tepal attachment, and 1 mm diameter at anther; color where fused with adaxial corolla between RHS 1C and RHS 4D, distally nearest RHS 187B, center nearest RHS 16D, and proximally above fusion nearest RHS 2C.

*Anthers*.—Oblong; dorsifixed, longitudinal; about 5 mm long and 2 mm wide; color nearest RHS N186A.

*Pollen*.—Abundant; less than 0.1 mm long; color nearest RHS 17A.

Fruit and seeds: Not observed;

Disease and pest resistance and tolerance: 'Rule of Plum' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage, but is able to tolerate some drought, when mature and direct sun without leaf burn when provided sufficient water.

Hardiness at least from USDA zone 3 through 9, and other disease resistance and tolerance is typical of that of other daylilies. The new plant is useful for landscaping en masse, as a single specimen or small groups.

I claim:

1. A new and distinct ornamental daylily plant named *Hemerocallis* 'Rule of Plum' as herein described and illustrated.

* * * * *